(12) United States Patent
Frost

(10) Patent No.: US 7,278,986 B1
(45) Date of Patent: Oct. 9, 2007

(54) SAFETY SYRINGE WITH NEEDLE

(76) Inventor: Robert J. Frost, 334 W. Michigan St., Lagrange, IN (US) 46761

( * ) Notice: Subject to any disclaimer, the term of this patent is extended or adjusted under 35 U.S.C. 154(b) by 387 days.

(21) Appl. No.: 11/075,994

(22) Filed: Mar. 9, 2005

(51) Int. Cl.
*A61M 5/32* (2006.01)
(52) U.S. Cl. .................................... 604/195
(58) Field of Classification Search ............ 604/181, 604/187, 192–198; 128/919
See application file for complete search history.

(56) References Cited

U.S. PATENT DOCUMENTS

| | | | |
|---|---|---|---|
| 4,767,413 A | 8/1988 | Haber et al. |
| 5,120,310 A | 6/1992 | Shaw |
| 5,122,118 A | 6/1992 | Haber et al. |
| 5,211,628 A | 5/1993 | Marshall |
| 5,338,304 A | 8/1994 | Adams |
| 5,376,080 A | 12/1994 | Petrussa |
| 5,385,551 A | 1/1995 | Shaw |
| 5,389,076 A | 2/1995 | Shaw |
| 5,578,011 A | 11/1996 | Shaw |
| 5,632,733 A | 5/1997 | Shaw |
| 6,015,438 A | 1/2000 | Shaw |
| 6,090,077 A | 7/2000 | Shaw |
| 6,272,870 B1 | 8/2001 | Gravin |
| 6,494,863 B1 | 12/2002 | Shaw et al. |
| 2002/0045843 A1 | 4/2002 | Barket et al. |
| 2004/0030294 A1 | 2/2004 | Mahurkar |

FOREIGN PATENT DOCUMENTS

EP 0596211 A1 5/1994

*Primary Examiner*—LoAn H Thanh
(74) *Attorney, Agent, or Firm*—Susan L. Firestone; Paul W. O'Malley

(57) ABSTRACT

A multi-use safety syringe has a retractable needle that retracts only when the user wants to retract the needle. The safety syringe has an internal moveable carriage that locks to an end cap with releasable locking elements. The safety syringe guards against premature retraction of the needle by requiring the simultaneous release of two releasable locking elements by the user. When the locking elements are released, the carriage is released. The released carriage slides backward within the barrel, retracting the needle within the barrel.

17 Claims, 4 Drawing Sheets

SAFETY SYRINGE WITH NEEDLE

BACKGROUND OF THE INVENTION

1. Field of the Invention

The present invention relates to a safety syringe with attached needle.

2. Description of the Prior Art

Used needles and syringes, especially extended needles, pose a risk of transmitting infectious diseases from accidental needle sticks. Contaminated needles and syringes can carry blood-borne infectious agents, such as gonorrhea and syphilis bacteria, as well as hepatitis and HIV viruses. While medical personnel and sanitation workers are at risk, the general population is also at risk from improper disposal of the used needle and syringe.

Prior art safety syringes with retractable needles have many problems. These problems relate to complexity, reliability, repeatability, cost and ease of use. Because syringes are mass produced at the rate of millions per day, cost is a significant factor in manufacture of the parts and the assembly of the device. Automated production of parts and assembly of parts is critical in order to have any hope of supplying a practical syringe to the market.

A major drawback of prior art single use syringes is that single use syringes cannot be used to clear air bubbles from the medicine, to inject fluid to mix medicine within a vial or to rinse the needle and syringe with a different medicine before filling with the desired medicine. In many of these devices once the plunger is plunger all the way forward, the plunger locks the needle and retracts the needle within the barrel to prevent a second use.

A need exists for a multiple use retractable syringe for health care and other workers. Health care workers typically push the plunger all the way forward before withdrawing fluid from a medicine vial. The worker then partially withdraws fluid from a vial into the syringe. The worker next flicks the syringe to free trapped air bubbles before plunging the air and at least some of the fluid back into the vial. This step clears air trapped within the barrel. After clearing out the air, the user withdraws the fluid for use.

Health care workers often first inject fluid into a vial of medicine in order to mix the medicine with the fluid. After mixing, the worker withdraws the mixed medicine from the vial for injection. Likewise, health care workers may first rinse the needle and vial with another medicine before inserting the needle into a medicine vial and withdrawing the medicine. After use, the worker can retract the needle into the syringe to prevent any risk of harm from the needle to others.

In a curious development, healthcare workers in the drug control field have expressed a need for a reusable retractable syringe to prevent the spread of blood borne diseases, such as AIDS and hepatitis. Such a syringe is preferably a full displacement syringe which will deliver essentially all of the contents without retracting and without limiting the ability of the user to draw a second dose. Hopefully the drug user will confine use to himself without sharing the needle but can retract the needle when finished and render the device inoperable.

The present invention is designed to accomplish these goals and more.

SUMMARY OF THE INVENTION

A multi-use safety syringe of the invention has a retractable needle that retracts when the user positively releases the needle. The safety syringe has a barrel with opposite plunger and end cap ends. Within the barrel is a carriage defined by a carriage wall extending axially from a radial base. An inward lip is located at one end of the carriage wall distal to the radial base. The needle attaches to the carriage and a spring abuts the carriage.

An end cap has a plug and a retainer adjacent to the plug. The plug engages the barrel at the end cap end and has a cylindrical sidewall. The retainer has a front wall opposite the plug and a pair of moveable locking elements located on opposite sides of the retainer.

Additional effects, features and advantages will be apparent in the written description that follows.

DETAILED DESCRIPTION OF THE INVENTION

Figure 1:
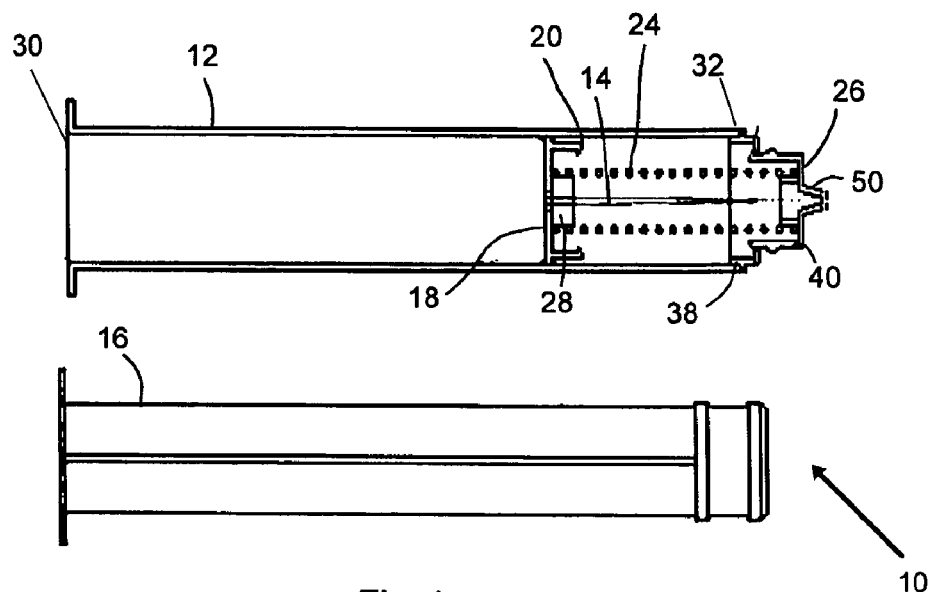
FIG. 1 is a sectional view of a syringe of the invention.
Figure 7:
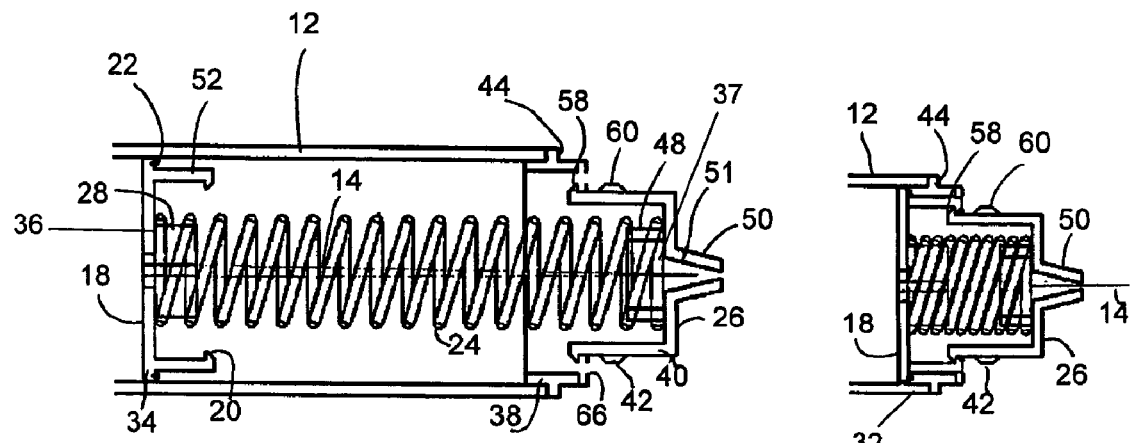
FIG. 7 is a partial side view of an unlocked carriage and end cap within the barrel of the invention and the needle retracted.
Figure 8:
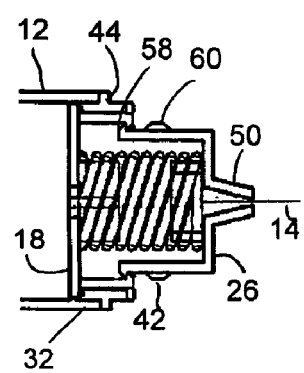
FIG. 8 is a partial side view of an locked carriage and end cap within the barrel of the invention.
Figure 2:
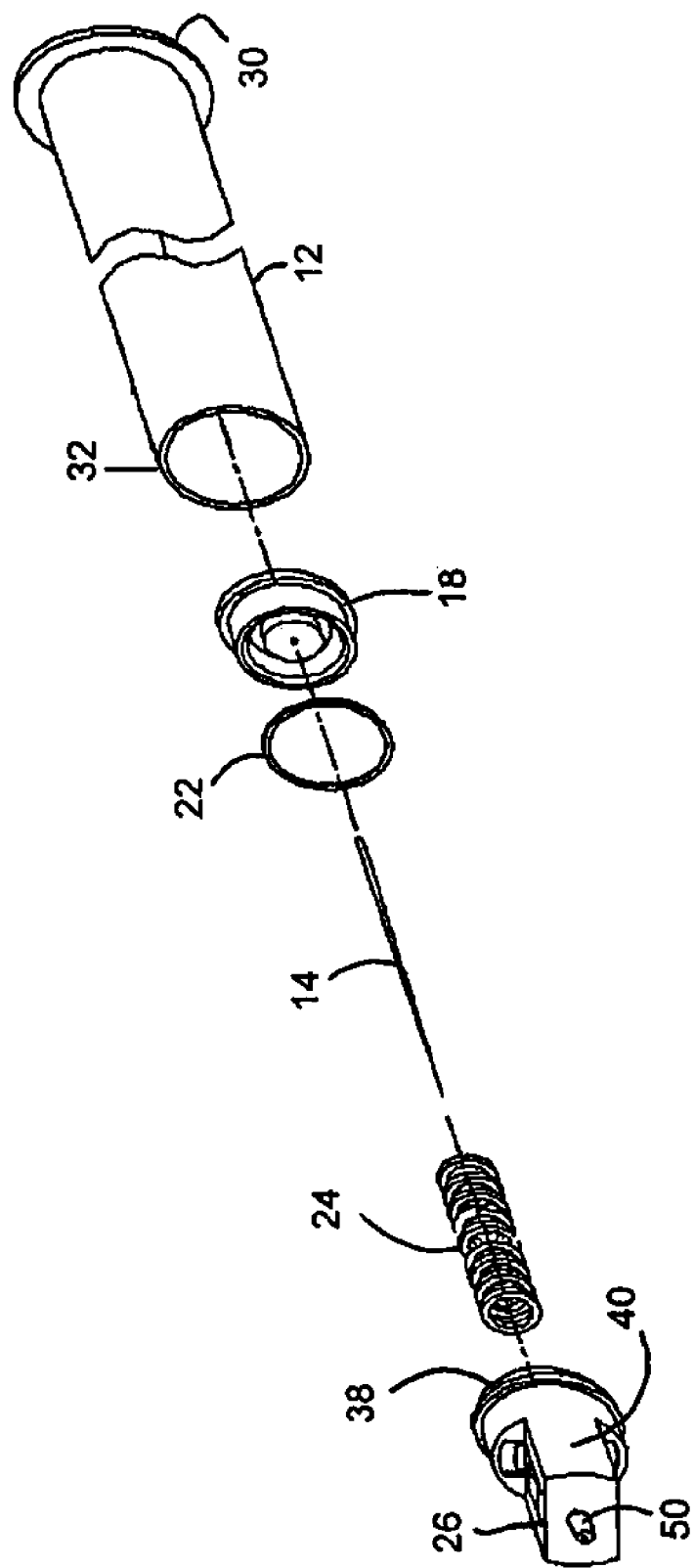
FIG. 2 is a perspective exploded view of a syringe of the invention.
Figure 3:
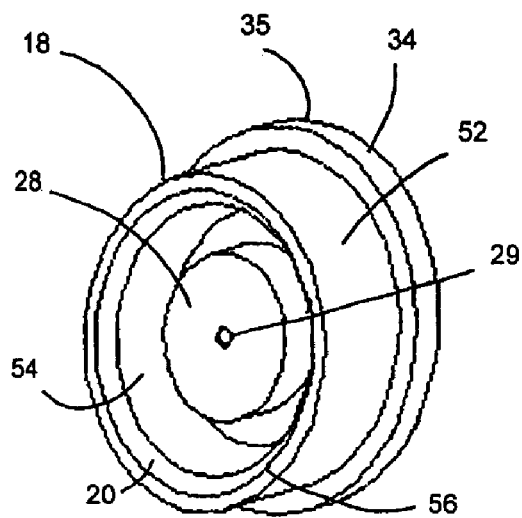
FIG. 3 is a perspective view of a carriage of the invention.
Figure 4:
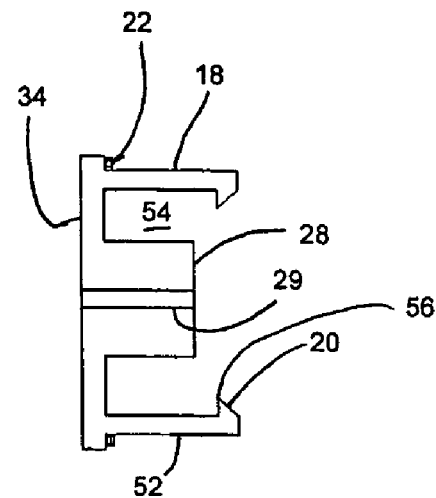
FIG. 4 is a longitudinal sectional view of the carriage of FIG. 3.
Figure 5:
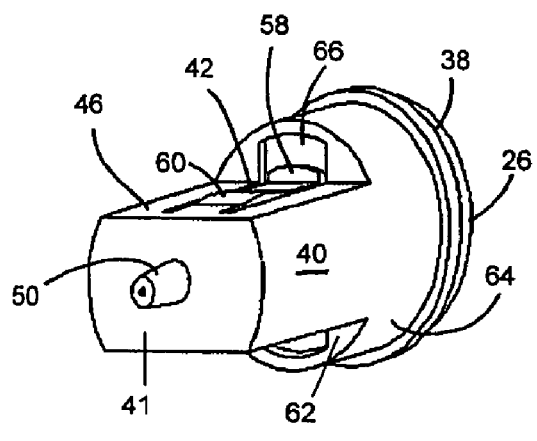
FIG. 5 is a perspective view of an end cap of the invention.
Figure 6:
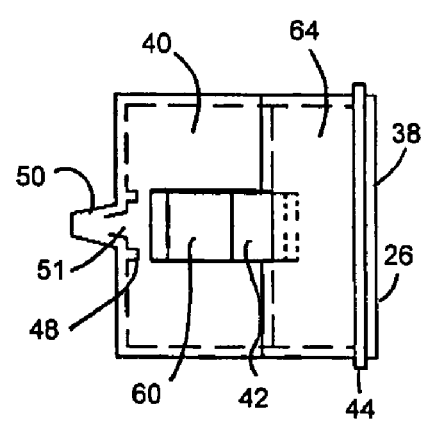
FIG. 6 is a top plan view of an end cap of the invention.

Turning to the Figures where like reference numerals refer to like structures, safety syringe 10 has barrel 12, plunger 16, end cap 26, carriage 18 and needle 14. Barrel 12 has an open plunger end 30 through which plunger 16 inserts. Opposite plunger end 30 of barrel 12 is an open end cap end 32 for receiving end cap 26. Carriage 18 releasably locks to end cap 26 during use.

A moveable carriage 18 slides within syringe barrel 12. Carriage 18 has a radial base 34 and carriage wall 52 extending axially from radial base 34. Inward lip 20 of carriage wall 52 is distal to radial base 34. While carriage wall 52 could be discontinuous, carriage wall 52 is preferably continuous and defines a chamber 54 and a mouth 56 located opposite radial base 34. Inward lip 20 of carriage wall 52 preferably borders mouth 56. A spring mount 28 can extend axially from the center of radial base 34 and is located within the carriage wall 52 and chamber 54.

Needle 14 attaches to the center of carriage 18, preferably attaching to spring mount 28. Needle 14 can attach by matingly engaging a needle lock, such as a luer lock having an interlocking nub and receiver, or by extending through an opening 29 in spring mount 28.

Seal 22 is located between carriage 18 and the interior wall of barrel 12. Seal can be an O-ring, washer, gasket, and the like, and is preferably around carriage wall 52 adjacent radial base 34.

The end cap 26 engages the barrel 12 at end cap end 32, preferably by partially fitting within the barrel 12. End cap 26 has plug 38 engaging barrel 12, retainer 40 adjacent to plug 38 and nose 50 projecting from front wall 41 outside of the retainer 40 at an end opposite plug 38. Retainer 40 has a pair of moveable locking elements 42 located on opposite sides of retainer 40 and which cooperatively engage lip 20 of carriage 18 when the syringe is in use. Each locking element 42 is part of retainer wall 46. Retainer wall 46 connects to front wall 41 and can be cylindrical, partially cylindrical with opposing flat walls and opposing curved walls or have flat walls. Locking element 42 has a tab 58 with angled head 59 and preferably a button 60 extending outwardly. The distance between locking elements 42 is preferably less than the distance between the carriage walls 56 or the diameter of chamber 54.

A nose hole 51 is in front wall 41 of retainer 40 and preferably is surrounded by nose 50. A cap spring mount 48 projects radially from the nose hole 51 within the retainer and preferably surrounds nose hole 51 opposite nose 50. Either cap spring mount 48 or nose 50 can have a pierceable membrane to seal the safety syringe 10 before use.

The plug 38 has cylindrical sidewall 64, end walls 62 adjacent to retainer 40 and cylindrical sidewall 64, and abutment ring 44 located on the exterior of cylindrical sidewalls 64. The end walls 62 are preferably on a plane perpendicular to the cylindrical sidewall 64 and the retainer wall 46, extending from an edge of the cylindrical sidewall 64 to the retainer 40. Cylindrical sidewall 64 matingly engages barrel 12. Cylindrical sidewall 64 preferably has a narrower diameter than barrel 12 and a wider diameter than carriage wall 52. Each end wall 62 has an aperture 66 into which locking element 42 and preferably tab 58 at least partially extends. Abutment ring 44 projects from sidewall 64 and abuts barrel 12 at end cap end 32.

A spring 24 is located between carriage 18 and end cap 26 and is preferably helical. Carriage end 36 of spring 24 abuts carriage 18, while opposite cap end 37 abuts end cap 26. Preferably, carriage end 36 surrounds spring mount 28 and cap end 37 surrounds cap spring mount 48 of end cap 26.

Figure 9:
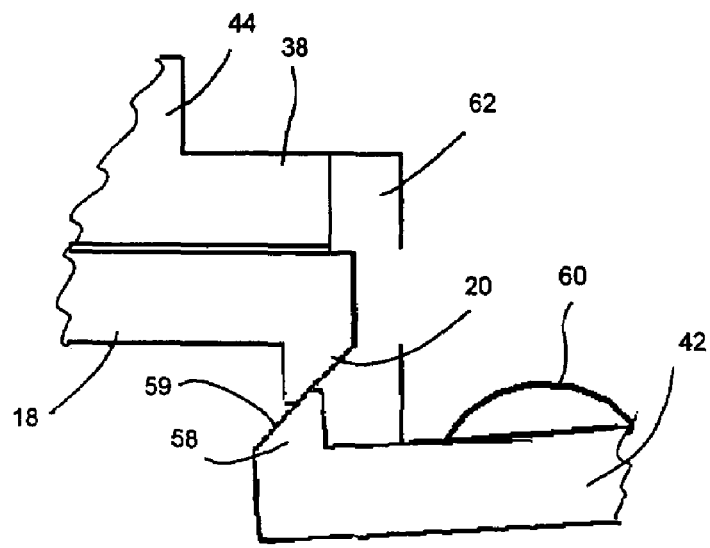
FIG. 9 is a close-up partial view of the tab and lip of the invention during engagement.
Figure 10:
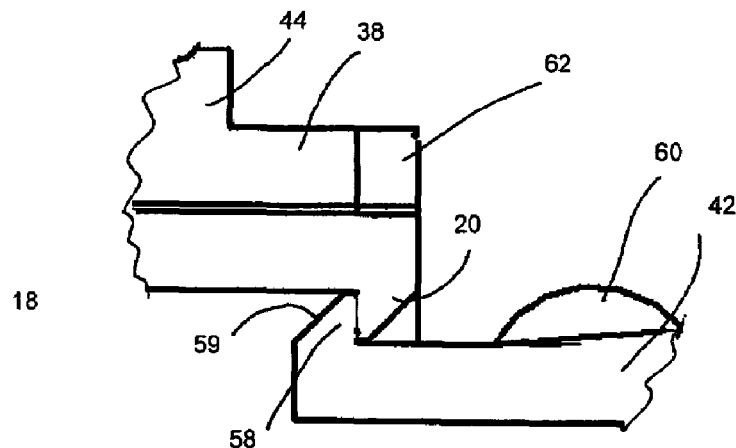
FIG. 10 is a close-up partial view of the tab and lip of the invention when the needle and carriage are locked.
Figure 11:
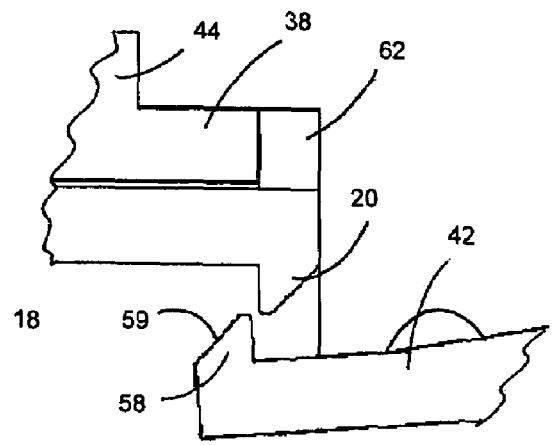
FIG. 11 is a close-up partial view of the tab and lip of the invention during disengagement.

To use the syringe 10, the user pushes plunger 16 forward. The plunger 16 in turn pushes carriage 18 forward until lip 20 on carriage 18 engages tabs 58 of end cap 26. As shown in FIGS. 8-11, the design of lip 20 complements the design of head 59 of tab 58, such as 45° angles. The complementary design allows lip 20 to slide past head 59 and force tab 58 inward (FIG. 9). Once lip 20 reaches the end walls 62 of plug 38, tab 58 returns to its initial position. The lower portion of lip 20 now locks against the upper part of head 59 and locks carriage 18, needle 14 and compressed spring 24 into position. At this point, needle 14 extends through nose 50 of end cap 26. If a pierceable material is used to make nose 50 or cap spring mount 48, needle 14 pierces the membrane while carriage 18 moves forward.

Plunger 16 can now be drawn back to fill barrel 12 of the safety syringe 10. To remove trapped air bubbles in the fluid or to mix the fluid within a vial, the user pushes plunger 16 forward to blow out air bubbles from the fluid in syringe barrel 12 and/or injects fluid into a vial. Carriage 18 remains locked to end cap 26.

Once finished with the syringe, the user simultaneously pushes both buttons 60 on tabs 58 of locking elements 42 to unlock the end cap 26 and carriage 18. This action pushes tabs 58 inwardly to disengage the heads 59 from lip 20. Once disengaged, the compressed spring 24 releases and pushes carriage 18 and plunger 16 backward within barrel 12. The retreating carriage 18 slides needle 14 through the nose 50, end cap 26 and into the barrel 12 with it, where the needle 14 remains safety retracted within barrel 12.

The safety syringe of the invention has a number of advantages. The syringe can be used for more than one use, thus allowing a user to clear air from the syringe before injection, mix medicine within a vial or pretreat the needle and syringe before drawing the desired medicine.

The syringe of the invention allows a one hand operation to retract the needle. This allows the user to have one hand free while retracting the needle.

Because the use of two tabs requires the user to simultaneously compress both tabs to retract the needle, this simultaneous operation prevents the premature retraction of the needle into the barrel if one tab is accidentally compressed.

If the carriage is color coded, such as green, the carriage shows through the aperture of the end cap, indicating that the carriage is securely locked into place and ready to use. This prevents the inadvertent use of the syringe before the needle is fully locked into position.

While the invention is shown in only one of its forms, it is not thus limited but is susceptible to various changes and modifications without departing from the spirit and scope of the invention.

What is claimed is:

1. A safety syringe, comprising:
   a barrel having a plunger end, and an opposite end cap end;
   a carriage within the barrel, the carriage having a radial base, and a carriage wall extending axially from the radial base;
   an inward lip at one end of the carriage wall distal to the radial base;
   an end cap having a plug engaging the barrel at the end cap end, the plug having a cylindrical sidewall;
   a retainer adjacent to the cylindrical sidewall of the plug;
   a front wall at an end of the retainer opposite the plug;
   a pair of moveable locking elements located on opposite sides of the retainer;
   a spring abutting the carriage; and
   a needle attaching to the carriage.

2. A safety syringe of claim 1, wherein the end cap further comprises:
   an end wall in the plug adjacent the retainer and the cylindrical sidewall; and
   an aperture in the end wall into which the locking element at least partially extends.

3. A safety syringe of claim 2, wherein the locking element further comprises:
   a tab having an angled head; and
   wherein at least part of the tab extends into the aperture.

4. A safety syringe of claim 3, wherein the tab further comprises:
   a button extending outwardly.

5. A safety syringe of claim 4, further comprising:
   a nose hole within the front wall of the retainer; and
   a nose projecting from the front wall outside of the retainer and surrounding the nose hole.

6. A safety syringe of claim 5, further comprising:
   a spring mount extending axially from a center of the radial base and engaging the needle; and
   a cap spring mount projecting radially from the nose hole within the retainer and surrounding the nose hole.

7. A safety syringe of claim 6, further comprising:
an abutment ring on the exterior of the cylindrical sidewall abutting the barrel at the end cap end.

8. A safety syringe of claim 7, further comprising:
flat retainer walls located on opposite sides of the retainer and containing the tabs.

9. A safety syringe of claim 8, further comprising:
a plunger within the barrel.

10. A safety syringe, comprising:
a barrel having a plunger end, and an opposite end cap end;
a plunger within the barrel;
an end cap having a plug engaging the barrel at the end cap end, the plug having a cylindrical sidewall;
a carriage within the barrel between the plunger and the end cap, the carriage having a radial base, and a carriage wall extending axially from the radial base;
an inward lip at one end of the carriage wall distal to the radial base;
a retainer adjacent to the cylindrical sidewall of the plug;
a front wall at an end of the retainer opposite the plug;
a pair of moveable locking elements located on opposite sides of the retainer and cooperatively engaging the inward lip of the carriage wall;
a compressed spring abutting the carriage and the end cap; and
a needle extending from the carriage and through the end cap.

11. A safety syringe of claim 10, wherein the end cap further comprises:
an end wall in the plug adjacent the retainer and the cylindrical sidewall; and
an aperture in the end wall into which the locking element at least partially extends.

12. A safety syringe of claim 11, wherein the locking element further comprises:
a tab having an angled head; and
wherein at least part of the tab extends into the aperture.

13. A safety syringe of claim 12, wherein the tab further comprises:
a button extending outwardly.

14. A safety syringe of claim 13, further comprising:
a nose hole within the front wall of the retainer; and
a nose projecting from the front wall outside of the retainer and surrounding the nose hole.

15. A safety syringe of claim 14, further comprising:
a spring mount extending axially from a center of the radial base from which the needle extends; and
a cap spring mount projecting radially from the nose hole within the retainer and surrounding the nose hole.

16. A safety syringe of claim 15, further comprising:
an abutment ring on the exterior of the cylindrical sidewall abutting the barrel at the end cap end.

17. A safety syringe of claim 16, further comprising:
flat retainer walls located on opposite sides of the retainer and containing the tabs.

* * * * *